US007726812B2

(12) United States Patent
Dai et al.

(10) Patent No.: US 7,726,812 B2

(45) Date of Patent: Jun. 1, 2010

(54) DEVICE FOR PREVENTING AND TREATING MYOPIA

(75) Inventors: Minghua Dai, Room 203, the Fourth Unit, Department of the twelfth middle school, No. 10 Fanguang Street, Shijiazhuang, Hebei, 050011 (CN); Yaodong Dai, Hebei (CN)

(73) Assignee: Minghua Dai, Shijiazhuang (CN)

(*) Notice: Subject to any disclaimer, the term of this patent is extended or adjusted under 35 U.S.C. 154(b) by 816 days.

(21) Appl. No.: 10/584,355

(22) PCT Filed: Dec. 20, 2004

(86) PCT No.: PCT/CN2004/015114

§ 371 (c)(1),
(2), (4) Date: Jun. 22, 2006

(87) PCT Pub. No.: WO2005/063153

PCT Pub. Date: Jul. 14, 2005

(65) Prior Publication Data

US 2009/0040459 A1 Feb. 12, 2009

(30) Foreign Application Priority Data

Dec. 25, 2003 (CN) ........................ 2003 1 0109716
Dec. 20, 2004 (CN) ........................ 2004 1 0098856

(51) Int. Cl.
*A61B 3/00* (2006.01)

(52) U.S. Cl. ...................................................... 351/203

(58) Field of Classification Search ................. 351/200, 351/203, 205, 210, 211, 212, 216, 222, 237, 351/238, 239, 243–246
See application file for complete search history.

(56) References Cited

U.S. PATENT DOCUMENTS 4,408,846 A * 10/1983 Balliet ........................ 351/203
5,231,430 A * 7/1993 Kohayakawa ............... 351/243
2006/0098164 A1* 5/2006 Blum et al. ................. 351/177

FOREIGN PATENT DOCUMENTS

| | | |
|---|---|---|
| CN | 2105947 | 6/1992 |
| CN | 2287026 | 8/1998 |
| CN | 2320226 | 5/1999 |
| CN | 1325666 | 12/2001 |
| CN | 2482398 | 3/2002 |
| RU | 2077253 | 4/1997 |
| RU | 2144341 | 1/2000 |
| TW | 561041 | 11/2003 |

* cited by examiner

*Primary Examiner*—Ricky L Mack
*Assistant Examiner*—Tuyen Q Tra
(74) *Attorney, Agent, or Firm*—Workman Nydegger

(57) ABSTRACT

A device for preventing and treating myopia includes a base, a spectacles frame (1), a holder (3) and a lens (2). The holder (3) is mounted on the base; a visual target (4) is placed on the base. The spectacles frame (1) is connected to the holder (3) by adjustable connecting parts (31,32,33,34,35), so the distance between the spectacles frame (1) and the visual target (4) which is placed on the base is adjustable.

16 Claims, 2 Drawing Sheets

DEVICE FOR PREVENTING AND TREATING MYOPIA

FIELD OF THE INVENTION

This invention generally relates to a vision physiotherapy correcting device, and more particularly to a device for correcting myopia with close de-focusing objects training.

BACKGROUND ART

Nowadays, ⅓ of the people in the world are suffering from myopia, and the situation is more and more serious. There are not ideal or effective devices for correcting myopia yet. In the past, Shen Zhen Weikang Technology Company produced the "Phoenix Eye 2000", which used red, blue and green vision frequency light to activate the retina and increase eyesight, but the effect is not satisfactory and slow. CN2081103U disclosed a normally worn lens for correcting nearsightedness, the upside of the lens is for correcting farsightedness while the downside is for correcting nearsightedness. However, it's difficult to focus on the object and make the reversed change to correct myopia or control the development, and the multi focus is bad for the youth's eyeball growth. In 1922, Sheard invented "far fogging" by wearing the convex in front of the eyes, which has some effects for correcting the myopia but can not reach a satisfied and stable result, so it couldn't be used widely. From 1980 to 1985, several primary school students had the experiment of wearing 1.5 D convex to read and write to correct myopia, which is the "near fogging" method. Actually this method can slow the myopia development a bit, but cannot correct it effectively. Some other therapeutic methods with convex have the same problem and cannot be spread for use.

SUMMARY OF THE INVENTION

The invention aims at providing a method and apparatus for particular myopia correcting for close de-focusing object training. It will be used particularly for short distance myopia correcting, with characteristics such as prominent effect, fast correcting, no side effect, simple structure, easy to extend, simple and scientific method. It is especially suitable for the usual prevention and cure of myopia for children and youth, as well as the fast cure of functional myopia.

The technology solution for the invention is: a myopia correcting apparatus particularly for short distance de-focusing object training, including the spectacles frame, lens frame and lenses. The characteristic is that the diopter of the lens is ($\Phi=1/u+A+B-\Delta\Phi$, while A is the rectified diopter of farsightedness, B is the de-focusing diopter with a select value between 0.1 and 3 D, $\Delta\Phi$ is the modified value, and u is the distance between viewed object and lens in the training. When the eyes are close to the lenses, $\Delta\Phi$ should be about zero, which equals to wearing the glasses; the reducing value $\Delta\Phi$ can be calculated by experiment; when the training position of eyes are far from the lenses, the lens diopter value $\Phi$ should also be reduced accordingly, to comply with de-focusing objects above; it can also be calculated according to relevant optical formula, such as $\Delta\Phi=[(1/u+A+B)^2u+2(1/u+A+B)+1/u]/(2+uA+uB+u/s)$, where s is the distance between lens and eye. The lenses can be defined as double eyes double lenses, double eyes single lens, or single eye single lens.

The distance between the object and lenses in the training, u, should be valued between about 130 and about 1000 mm.

To improve the applicability and convenience of training reading and writing, the distance (u) between the object and lenses in the training should be valued between about 200 and about 500 mm with priority.

To be more applicable and general as well as to improve the prevention effect, the distance (u) between the object and lenses in the training above should be valued between about 250 and about 330 mm with priority.

There are distance-control mechanisms such as sound, light, electrical, mechanical, or manual mechanism for the distance (u) between the object and lenses in the training. The mechanism should be able to control the distance between the object and lenses in the training to be within the u value range, in order to keep the eyes in the condition that they can be trained and relaxed at the same time. To train eyes relaxation, activate the dim adjusting and vision distance adjusting change well or readily by controlling or adjusting distance.

The mechanical distance-control mechanism should be in fixed or adjustable desk frame; the structure should be simple, stable, and convenient. The lens frame is better to be desk frame, which means fixed or adjustable desk frame distance-control structure, or adorn spectacles frame and glasses (such as glasses with stands or headgear), and there should be a distance-control ruler, or other flexible measurement control, on it.

It is better to set a loading plate (or platform) under the fixed and adjustable desk frame, where visible objects such as a vision mark can be put. The loading platform should be configured with up and down mechanism, to help trainers adjust the position for easily training.

The lenses can be single lenses or equivalent diopter compound lenses. With a view to a better effect, the lenses should be compound lenses which include ocular and object lenses. The ocular is $\Phi2$ convex, the object lens is $\Phi1$ concave mirror, the distance between the ocular and object lenses should be fixed or adjustable, which can be calculated with the formula $\Phi=(\Phi1+\Phi2-\Phi1\Phi2\Phi d)/1-\Phi1d$ (d is the distance between ocular and object lenses); at this time u should be the distance between the viewed object and ocular in training; the light blocker can be added between the ocular and object lenses. The lenses can also be alternative series lenses or focus-adjustable lenses.

The viewed objects in question could also be books. To improve the eye accommodation training effect in proper space frequency, the special vision mark is favorable for the above-mentioned viewed object.

The above-mentioned special vision mark may consists of line drawings, regular letters, numbers or characters (i.e. article) of different or the same size, such as a graphic micro-vision chart or a booklet of vision marks.

The special vision mark could be an LCD screen of a play station with consideration for increase of interests and attention of the patient, improvement of the vision psychological effect, insurance of the training time or the combination of learning and reading training.

The above-mentioned special vision mark may be a single vision mark for double eye or single eyes; however, double vision marks are preferred. Double vision marks are in paralleled, placed for double eye double lens coincidence, which is easy for double eye coincidence training and convenient for double eye parallel sight, resulting in the reduction of the concentration and the convergence adjustment of double eyes to help the eyes relaxation, adjustment, and change of farsightedness. The center to center distance between the two vision marks is between about 20~about 100 mm, and the two vision marks could be the same or different, which is judge by the principle of convenient coincidence.

For the improvement of correcting effect in single vision coincidence training, the concentration and convergence adjustment of double eyes should be minimized to help the eyes relaxation, adjustment, and change of farsightedness; or for the better formation of double vision marks. The above mentioned two lenses should be with a composite prism towards to the sides of nose or inner downward, the degree of prism $P=3^{\Delta}\sim15^{\Delta}$ to be better, also can be $P=50\times d_1/u$, where $d_1$ is the distance between eyes for far sight, u is the distance between the vision mark and the front lens; or the two lenses can be two de-centered lenses.

To prevent the near perceived accommodation of human eyes, the blockers can be placed around the lens within the device for concentration and better effect. In the case of the double vision mark, a mechanism to avoid sight intersection can be added, such as a vertical sight spacer (or barn door), to prevent the sight interference caused by eye sight's crossed diplopia.

The method with the adoption of myopia correcting apparatus particularly for short distance de-focusing object training, includes:

A is confirmed for the nearsightedness degree of trainee.

Select the value of distance (u) between viewed object and lens in training referring to the habit and necessity for short-distance work and study.

Choose a value for B and ΔΦ;

With the above-mentioned values of A, u, B and ΔΦ, the value of diopter Φ can be calculated via the formula $\Phi=1/u+A+B-\Delta\Phi$ for selection of the training apparatus;

Place a viewed object in front of the lens, and set the distance between the viewed object and lens as u; Adjust the distance (u) between the object and lenses with the means of sound, light, electrical, mechanical, or manual methods at the time of training.

Trainee observes the viewed object in question through the said lens and repeats above training until a clear vision of the viewed object can be obtained.

Repeat above procedures with gradual increase of diopter Φ of lens. Through the training, the trainee sight could be expected to reach the desired status step by step; Provided there are no changes upon the diopter Φ of lens, through the regulation of u, the de-focusing object training still can be performed referring to the formula and the renewed A.

Thus, this method is designed based on the diopter of the lens, $\Phi=1/u+A+B-\Delta\Phi$, ΔΦ is the revised value; when the eyes are close to the lens, at this time, equivalent to the adorn spectacles; when the eyes are far away from the lens in training, the diopter Φ of lens should be decreased accordingly to produce the same effect of as above of de-focusing the object (decreasing the ΔΦ obtained from the experiment); also can be calculated from relevant optical formula, such as $\Delta\Phi=[(1/u+A+B)^2u+2(1/u+A+B)+1/u]/(2+uA+uB+u/s)$, where S is the distance between the lens and the eyes. The training distance should be determined first for the distance (u) between the viewed object and the lens with respect to the necessity of working and studying in short distance, that is the distance (u) between the viewed object and the lens for training. The range of u is within about 300~1000 mm, about 200~500 mm, or about 250~330 mm. B value is still required, which is determined by the difficulty for the judgment of the viewed object, in the case of hard to distinguish, choose the lower limit, if comparatively easier, choose the upper limit; determine Φ by the formula $\Phi=1/u+A+B-\Delta\Phi$; under this rule, exercise the de-focusing training cure in the event of working and studying in short distance. In the case of sight recovery, for the further sight improvement, the distance (u) between the viewed object and the lens in training can be adjusted according to the formula and the recovered A to keep on the de-focusing object training, or change Φ by the formula $\Phi=1/u+A+B-\Delta\Phi$ and u can be held constant and keep on the de-focusing object training with the recovered A and the formula. By using distance-control mechanisms such as sound, light, electrical, mechanical, or manual mechanism to adjust the distance (u) between object and lenses in the training.

The design and cure mechanism of the invention is: this invention is designed particularly for the short distance training, reading, and writing, to frequently maintain the eyes at the status of de-focusing, that is to say, the formation focus is within vitreous rather than retina, the de-focusing vision formed on the retina discontinuously activates the blur adjustment and far vision adjustment of human eyes. Such long term exercise can fulfill the goal to prevent and cure nearsightedness.

The static diopter of normal eyes can make the parallel-entered sight focus on the retina and without dynamic refraction adjustment. For the recovery of the function, the long time of near diopter accommodation should be avoided and the parallel sight is preferred. While for the patient of myopia, the ciliary muscle of eyes is in spastic condition, and it is very obvious in the experiment that only the reduction of near vision accommodation cannot work, when the eye is in the state of de-focusing the object for far vision, that is to produce the far vision "blur adjustment" through the lens and the formation of eyes diopter system within the vitreous in front of the retina, as a result, the ciliary muscle can be relaxed toward the normal condition and the spastic state can be released fast and effectively. Therefore, only convex lens of low degree applied in short distance to reduce the eyes accommodation is useless. Even when convex lenses of medium and low degree are applied, and near vision observation is performed liberally with the absence of consideration for the distance of the viewed object, the ideal or reliable effect cannot be guaranteed; the specific distance for the use is the first thought. The effective de-focusing object can be achieved through the match of the specific lens to the right distance. The diopter B of de-focusing should be within about 0.1~3 D or about 0.25~3 D; if less, e.g. about 0.1~1 D, easy to distinguish, clear feeling and suitable for long time training and learning; if less than about 0.1 D, none of the de-focusing might occur because the reversed adjustment therapy cannot be activated; if too large, e.g. about 2~3 D, the blur feeling is smart, too more training load, eye strain easily arises, so the period for training should not be too long; if larger than about 3 D, unable to distinguish because of de-focusing too lager, the learning and training is not applicable and further more, empty-space myopia might occur, it should also be avoided; around about 1 D is OK for general condition. That is the prevention and cure mechanism for the de-focusing object. For the rigid constraints on the distance for use, only manual control is still not enough. The distance-control mechanism is designed to meet the requirement. In the beginning, people feel that the vision mark is not clear enough, however, after watching for a long time and concentrating, the object becomes more clear and obvious. That is the process of far vision accommodation. It can promote the eyes to dynamically adjust the diopter to be zero or reversely change, and suspend the growth of axis oculi and enhance the capability of far vision accommodation through the de-focusing image on the retina, which leads to the farsightedness, so the prevention and cure to the structural myopia can be realized. Shoeffel and schmid used convex lenses and concave lenses on chicken eyes to perform the de-focusing experiment of animal eyes in 1998 and 1996 respectively. The success of treating animal farsightedness and nearsightedness provides the evidence of anatomy experiment that the de-focusing object can change the diopter and sightedness of animals.

Vision mark effect is to make the patient concentrate on the reading therapy. It can activate the interest and enthusiasm of patient in training, with the use of different vision space frequency and the symbols of various difficulty to identify in the exercises, which guides the patient intentionally towards to the symbols that are hard to identify, consequently the virtuous accommodation of eyes might occur to trigger the enthusiasm of the patient for therapy, that is in the light of the principle of psychology and vision biology.

The major factors for myopia are: (1) Genetic and evolutionary factors; and (2) Environmental factors. The genetic factor is the inner cause from the human and is unchangeable, which determines the potential for the occurrence and development of myopia, while it is also affected and activated by the environmental factors. The environmental factor is the outer cause, the eyes are the light sensor, which are changed and developed according to the exterior light situation. Emitting light from the near environment results in near vision adjustment; the parallel light of far vision and the de-focusing on the sides of vitreous in front of the retina bring forward the reverse change. Long term near vision and less far vision make the inner cause effect and result in the development and genetic change of nearsightedness as eye compensation. So the environment and light are the key cause to the disease, as well as the key for the prevention and cure. Thus the change of environment is a must, from near vision to far vision (or simulating far vision to change the emitting angel of light in eyes), it can develop the potential for farsightedness and suspend the nearsightedness.

When the healthy eyes watch the far point, eyes adjustment is relaxed and the concentration of eyes is zero, the viewed object is formed at the fovea of eyes; in the case of near point, the concentration and adjustment of eyes are interacted accordingly to keep the formation of single eye and center vision. The change upon the environment for the use of the eyes and the unreasonable use of the eyes, the biologically unqualified use begins particularly from childhood, resulting in the decreased chance of far sight, which causes the human optic nervous system to be more and more adaptable to the emitting light of near vision, and resulting in the fast growth and development of nearsightedness.

The multiple animal experiments on chickens, infant monkeys, and cats, anatomy research and a mountain of statistical materials of nearsightedness principles have provide a firm ground: the major cause of nearsightedness is resulted from long term near vision. In contrast, if long time eye concentration and positive adjustment can be avoided and do more reverse adjustment to produce the compensation, it is helpful to prevent and cure the myopia.

From the view of ophthalmology neurology theory, the concentration and the adjustment of human eyes and the constriction of the pupils are correlated, and according to the Donders line we can know when the concentration of emmetropia is zero, the corresponding adjust is zero, so in the case of larger concentration, the larger the adjustment is. The reason of accommodative myopia is just the near vision for a long time and over concentrated and adjustment, as a result the adjustment is of no use for relaxation and the mismatch of adjustment and concentration. After the change of concentration to zero through human adjustment, then the de-focusing training will promote the adjustment to be zero to comply with the original corresponding principle. Such training can let the adjustment return to normal, and return to original collocation rule so that it can prevention and cure the myopia. The effect of the Double vision marks combine with the triangular prism can achieve this purpose.

A lot of practices reveal that the prominent effect and the characteristics of the invention are: be particular for myopia correcting training, with characteristics such as, fast correcting, safe and reliable, simple structure, no side effect, easy to extend, simple and scientific method. Generally, most child myopia can be improved to about 1.5 within about 3 months.

Accompanied with the diagrams, the detailed description of implementation is given below, but this invention is not limited by this.

In FIGS.: 1—Blocker Spectacle Frame 2—Double Convex Lenses 3—Adjustable Desk Frame 4—Micro LCD Gameboy Screen Single Vision Mark 6—Tri-lever Adjustable Support 7—Double Vision Marks 8—Anti Eye Sight Interleave Spacer 9—Single 4 D Convex Lens 10—Bio-lever Adjustable Support 11—Book Single Vision Mark 12—Distance-Control Ruler 13—Single Vision Mark 14—Stands Frame 15—Mobile restricting lens and monochromatic lens 16—Anti Eyes Sight Interleave Reflection Blocker Baffle 17—Therapeutic Pull Rod Telescopic Distance-Control Ruler Connected to Spectacles 18—Interior Built Vision Mark Illumination Monochromatic Light 19—Loaded with Two Same Parallel Micro Eye Chart Transparent Vision Mark Box 31—Adjusting Hand Wheel 32—Pinion 33—Track Slide 34—Rack 35—Cone Screw

DETAILED DESCRIPTION

Figure 1:
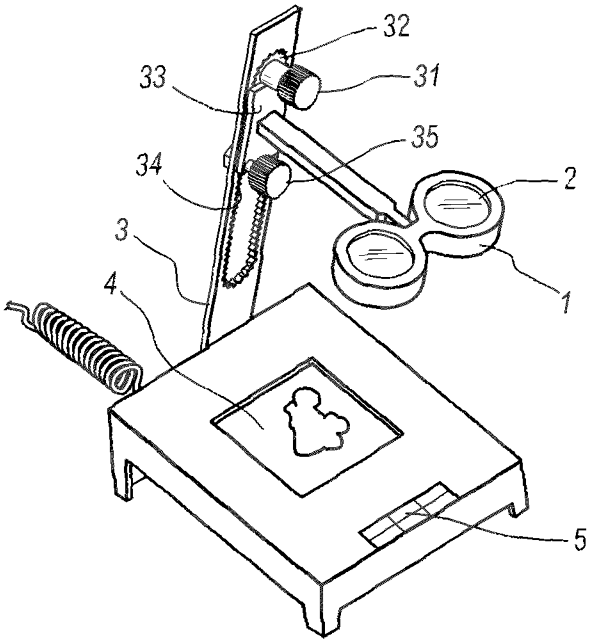
FIG. 1 shows the schematic view of double lenses single vision mark desk cure apparatus of this invention.

As shown in FIG. 1, 1 is blocker frame, double convex lenses 2 are 4D9Δ, mode distance-control is adjustable desk frame 3: Track and rack 34 and track slide 33 are on the support; Pinion 32 and rack 34 are in mesh; Pinion 32 is connected with track slide 33 through axis lever; the support of track slide 33 is connected with blocker frame 1; Adjusting hand wheel 31 is on the axis lever of pinion 32 to lift and drop the pinion 32 along with rack 34; Adjusting cone screw 35 on track slide 33 is to adjust the frication between track slide 33 of belt fasten structure and the tracks to slide or lock; 4 is micro LCD game screen single vision mark; 5 is the control key of LCD gameboy; According to the formula $\Phi=1/u+A+B-\Delta\Phi$, when A is about −1.00 D, B is about 2 D, $\Delta\Phi$ is about zero, u is about 330 mm. If A is about −3.00 D, other values unchanged, the double convex lens 2 can be replaced with 2D9Δ; if A is about −3.00 D, the double convex lens 2 is 3D9Δ, the value of u will be about 250 mm, others will not be changed.

Figure 2:
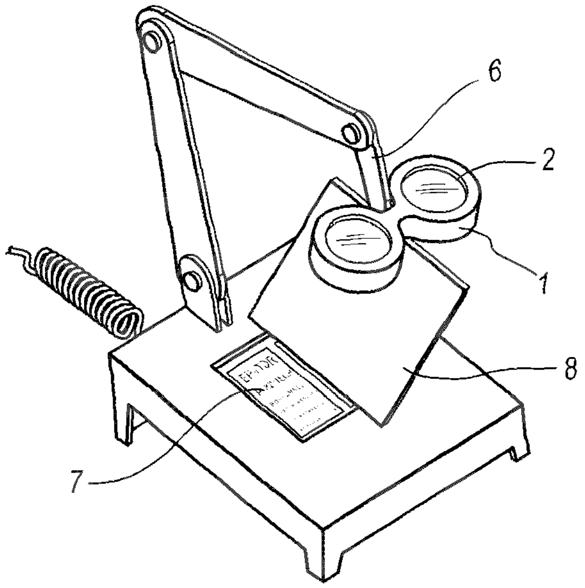
FIG. 2 shows the schematic view of double lenses double vision marks desk cure apparatus of this invention.

As shown in FIG. 2, the double convex lens 2 is about 10 D, the mechanical distance-control is tri-lever adjustable support 6, the double vision marks 7 are on the desk plate, a vertical anti eyes sight interleave baffle 8 is set in the middle of two lenses; if u is about 130 mm, B is about 3 D, thus A can be about −0.7 D.

Figure 3:
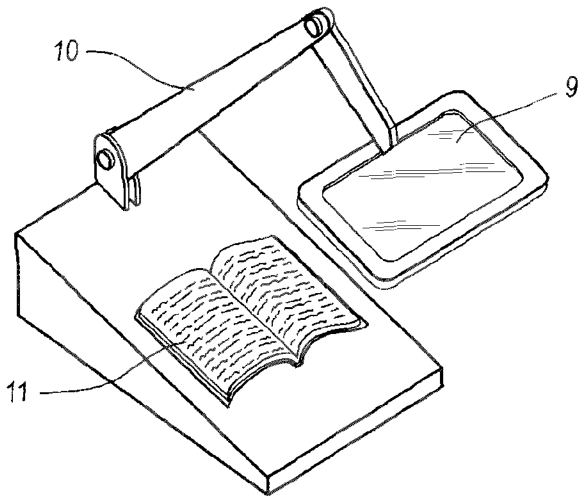
FIG. 3 shows the schematic view of single lens single vision mark desk cure apparatus of this invention.

As shown in FIG. 3, 9 is about 4 D convex lens single let, mechanical distance-control is bio-lever adjustable support 10, the book single vision mark 11 is on the desk plate; either single eye or both eyes training is applicable; if u is about 200 mm, B is about 3 D, thus A can be about −4 D.

Figure 4:
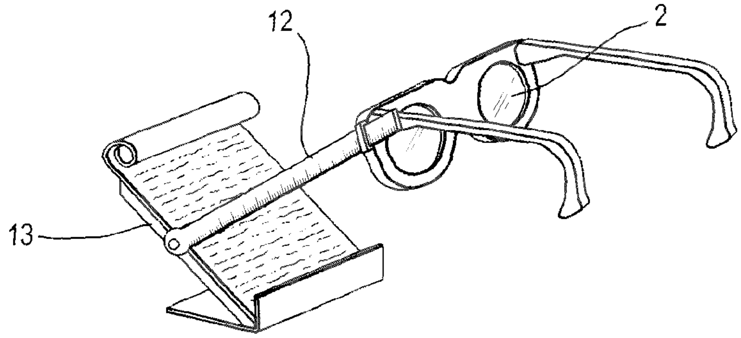
FIG. 4 shows the schematic view of double lenses single vision mark adorn spectacles cure apparatus of this invention.

As shown in FIG. 4, the double concave lens 2 is about 3.5 D3Δ standing frame, mechanical distance-control is distance-control ruler 12 which is connected to the single vision mark plate 13; if u is about 1000 mm, B is about 3 D, thus A can be about −0.5 D.

Figure 5:
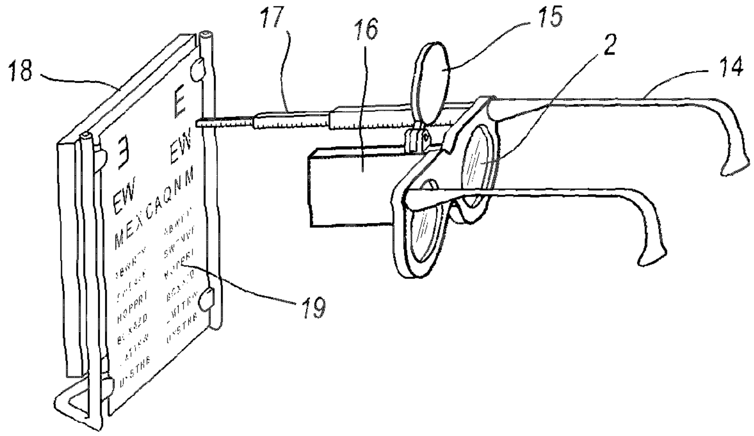
FIG. 5 shows the schematic view of double lenses double vision marks adorn spectacles cure apparatus of this invention.

As shown in FIG. 5, the double concave lens 2 is about −2 D, 14 is standing frame, the anti eyes cross sight reflection blocker baffle 16 is set in the middle of two lenses 2, the mobile restricting lens 15 is placed between two lenses 2 and blocker baffle 16 for the ease of single eye training. Mechanical distance-control mechanism is the therapeutic pull rod telescopic distance-control ruler 17, 19 is the transparent vision mark box which is loaded with two same parallel micro eye charts, 18 is interior built vision mark illumination monochromatic light; if u is about 500 mm, B is about 1 D, thus A can be about −5 D. Training should be performed in the light of above stated methods. Interior Experiment Condition.

The number of people to be tested; Testing object: children (boys and girls); Age: about 6~14 years old; the degree of myopia is about 0.06~0.8; training method: unified training about once or twice a week, about 2 hours each, individual about 1.5 hour training at home, lasting for a year. Standard: by measuring farsightedness according to the international standard, and adopting the retinoscopy to improve 3 behavior effectiveness, about 1.0 or above means recovery (cured); the unit to perform the interior experiment: some pediatrics academy.

For the result of therapeutic experiment, please refer to Diagram 1.

For the therapeutic instance of students who join in the training after receiving dilated pupil therapy, please refer to Diagram 2.

TABLE 1

| total amount of eyes (unit) | effective (unit) | percentage of effect (%) | cure (unit) | percentage of cure (%) | length of myopia | age (year) |
|---|---|---|---|---|---|---|
| 280 | 269 | 96 | 191 | 68 | one year and above | 6~14 |
| 200 | 200 | 100 | 170 | 85 | less than one year | 6~14 |

TABLE 2

| serial number | name | degree of right eye before treating | degree of left eye before treating | degree of right eye after treating | degree of left eye before treating | improved number of rows right | improved number of rows left |
|---|---|---|---|---|---|---|---|
| 1 | Zhang xx | 0.15 | 0.15 | 0.5 | 0.5 | 5 | 5 |
| 2 | Liu xx | 0.15 | 0.10 | 1.0 | 1.0 | 8 | 10 |
| 3 | Zhong x | 0.25 | 0.6 | 1.0 | 2.0 | 6 | 5 |
| 4 | Liu xx | 0.15 | 0.25 | 0.8 | 0.8 | 5 | 5 |
| 5 | Luo xx | 0.1 | 0.06 | 0.5 | 1.0 | 10 | 11 |
| 6 | Hao xx | 0.1 | 0.25 | 0.4 | 0.6 | 6 | 4 |
| 7 | Wang xx | 0.25 | 0.4 | 0.8 | 0.8 | 5 | 3 |
| 8 | Zhou xx | 0.12 | 0.2 | 0.8 | 0.8 | 8 | 6 |
| 9 | Li xx | 0.5 | 0.5 | 1.2 | 1.2 | 4 | 4 |
| 10 | Hao xx | 0.25 | 0.5 | 1.0 | 0.8 | 6 | 2 |
| 11 | Liu xx | 0.2 | 0.15 | 1.0 | 1.0 | 7 | 8 |
| 12 | Zhang x | 0.12 | 0.12 | 0.5 | 0.5 | 6 | 6 |
| 13 | Ma xx | 0.3 | 0.25 | 1.0 | 1.0 | 5 | 6 |
| 14 | Ling xx | 0.25 | 0.25 | 2.0 | 2.0 | 9 | 9 |
| 15 | Li xx | 0.4 | 0.25 | 0.8 | 0.5 | 3 | 3 |
| 16 | Jun xx | 0.15 | 0.25 | 0.6 | 0.6 | 6 | 4 |
| 17 | Duan xx | 0.15 | 0.12 | 0.5 | 0.5 | 5 | 6 |
| 18 | Gao xx | 0.15 | 0.2 | 0.6 | 0.6 | 6 | 5 |
| 19 | Qiao xx | 0.4 | 0.3 | 0.8 | 1.0 | 3 | 5 |
| 20 | Liu xx | 0.12 | 0.6 | 0.3 | 1.2 | 4 | 3 |
| 22 | Wang xx | 0.25 | 0.2 | 0.5 | 0.5 | 3 | 4 |
| 22 | Zhang xx | 0.25 | 0.3 | 0.6 | 0.6 | 4 | 3 |
| 23 | Liang xx | 0.06 | 0.1 | 1.0 | 1.2 | 11 | 11 |
| 24 | Feng xx | 0.25 | 0.3 | 0.6 | 0.8 | 4 | 4 |
| 25 | Ren xx | 0.12 | 0.2 | 0.3 | 0.4 | 4 | 3 |
| 26 | Li xx | 0.15 | 0.2 | 0.4 | 0.4 | 4 | 3 |
| 27 | Xing x | 0.8 | 0.6 | 1.5 | 1.2 | 3 | 3 |
| 28 | Tuo xx | 0.15 | 0.2 | 0.8 | 0.8 | 7 | 6 |
| 29 | Yuan xx | 0.25 | 0.2 | 1.2 | 1.2 | 7 | 8 |
| 30 | Li xx | 0.12 | 0.12 | 0.6 | 0.6 | 7 | 7 |
| 31 | Zhang xx | 0.8 | 0.8 | 2.0 | 2.0 | 4 | 4 |
| 32 | Liu xx | 0.3 | 0.25 | 0.8 | 0.8 | 4 | 5 |
| 33 | Ren x | 0.25 | 0.25 | 1.0 | 1.0 | 6 | 6 |
| 34 | Ma xx | 0.2 | 0.2 | 0.6 | 0.6 | 5 | 5 |
| 35 | Liu xx | 0.6 | 0.5 | 1.2 | 1.2 | 3 | 4 |
| 36 | Li xx | 0.4 | 0.3 | 1.0 | 0.6 | 4 | 3 |
| 37 | Guo xx | 0.4 | 0.8 | 0.8 | 1.5 | 3 | 3 |
| 38 | Liu xx | 0.4 | 0.5 | 1.2 | 1.2 | 5 | 4 |

The invention claimed is:

1. A device for preventing and treating myopia, the device comprising:

a frame having an object associated therewith, a spectacles frame coupled to said frame, and two lenses coupled to said spectacles frame, wherein the diopter value (Φ) of said lenses is governed by the equation $\Phi=1/u+A+B-\Delta\Phi$, wherein "A" the degree of myopia which is negative and reflects the diopter of distance vision correcting, "B" is the degree of focus-out diopter and has a value between 0.1~3 D, "ΔΦ" is the adjust value, and "u" is the distance between the object and said lenses.

2. The device for preventing and treating myopia as defined in claim 1, wherein the value of "u" is between 130 mm~1000 mm.

3. The device for preventing and treating myopia as defined in claim 1, wherein the value of "u" is between 200 mm~500 mm.

4. The device for preventing and treating myopia as defined in claim 1, wherein the value of "u" is between 250 mm~330 mm.

5. The device for preventing and treating myopia as defined in claim 1, wherein there are distance-control mechanisms such as sound, light, electrical, mechanical or manual mechanisms for establishing the distance "u" between the object and said lenses.

6. The device for preventing and treating myopia as defined in claim 5, further comprising a table-frame of spectacles, wherein said table-frame of spectacles is a machine controlled device configured to be fixed or adjustable.

7. The device for preventing and treating myopia as defined in claim 6, further comprising a loading platform under said table-frame of spectacles and an elevator coupled to the loading platform.

8. The device for preventing and treating myopia as defined in claim 1, wherein said lenses are knockdown lenses said knockdown lenses each comprising an eyepiece and an objective, wherein said eyepiece is a convex lens, and said objective is a concave lens.

9. The device for preventing and treating myopia as defined in claim 1, wherein said lenses comprise a substitutable series lens or a focus-adjustable lens.

10. The device for preventing and treating myopia as defined in claim 1, wherein the object is a special visual object.

11. The device for preventing and treating myopia as defined in claim 10, wherein the object is a game machine's LCD.

12. The device for preventing and treating myopia as defined in claim 10, wherein the object is a double viewed object and is paratactic so imaging can be formatted binocularly by double lenses.

13. The device for preventing and treating myopia as defined in claim 10, wherein said lenses each comprise a triangular prism having a degree of triangular prism of between about 3 and about 5 prism degrees, and said special visual object is a single vision mark.

14. A method for treating required close de-focusing object training myopia using a device, the method comprising the steps of:

providing the device that includes a frame having an object associated therewith, a spectacles frame coupled to said frame, and two lenses coupled to said spectacles frame, wherein the diopter value (Φ) of said lenses is governed by the equation $\Phi=1/u+A+B-\Delta\Phi$, wherein "A" the degree of myopia which is negative and reflects the diopter of distance vision correcting, "B" is the degree of focus-out diopter and has a value between 0.1-3 D, "ΔΦ" is the adjust value, and "u" is the distance between the object and said lenses, providing the object between said frame and the front of said lenses, adjusting the distance between the object and said lenses to "u"; and adjusting the distance "u" with sound, light, electrical, mechanical or manual mechanism.

15. The method as defined in claim 14, further comprising the step of adjusting the diopter Φ value and then repeating the steps set forth in claim 14.

16. The method of claim 15, wherein if the diopter Φ of the lens is varied by adjusting the distance (u) between the viewed object and the lens in the training.

* * * * *

UNITED STATES PATENT AND TRADEMARK OFFICE
CERTIFICATE OF CORRECTION

PATENT NO. : 7,726,812 B2
APPLICATION NO. : 10/584355
DATED : June 1, 2010
INVENTOR(S) : Dai et al.

It is certified that error appears in the above-identified patent and that said Letters Patent is hereby corrected as shown below:

Column 1
Line 18, change “light” to --lights--
Line 26, change “convex” to --convex lens --
Line 30, change “convex” to --convex lens--
Line 34, change “convex” to --convex lens--
Line 55, change “between viewed object and lens” to --between the viewed object and the lens--

Column 2
Line 10, change “mechanism” to --mechanisms--
Line 18, after “in” insert --a--
Line 20, after “be” insert --a--
Line 21, after “means” insert --a--
Line 29, before “up and down mechanism” insert --an--
Line 30, change “easily” to --easy--
Line 47, change “consists” to --consist--
Line 49, before “article” insert --an--
Line 52, before “increase” insert --an--
Line 54, change “effect” to --effects--
Lines 58-59, change “paralleled” to --parallel--
Line 66, change “judge” to --judged--

Column 3
Line 1, before “correcting” insert --the--
Line 7, before “nose” insert --the--
Line 9, before “eyes” insert --the--
Lines 19-20, before “myopia correcting apparatus” insert --the--
Line 24, before “viewed object” insert --the--
Line 27, change “;” to --.--.
Line 30, change “apparatus;” to --apparatus.--
Line 39, change “Repeat above procedures” to --Repeat the above procedures--
Line 39, change “of diopter” to --of the diopter--

Signed and Sealed this

Fourteenth Day of December, 2010

David J. Kappos

David J. Kappos
*Director of the United States Patent and Trademark Office*

Line 41, change “Provided” to --provided--
Line 52, change “from relevant” to --from the relevant--
Line 53, change “where S is” to --where s is--

Column 4
Line 7, change “mechanism” to --mechanisms--
Line 29, change “of eyes” to --of the eyes--
Line 40, change “match” to --matching--
Line 47, change “too more training load” to --too much training load--
Line 49, change “lager” to --largely--
Line 52, change “condition” to --conditions--
Line 64, change “to the farsightedness” to --to farsightedness--
Line 65, change “cure to the structural myopia” to --cure to structural myopia--
Line 66, change “schmid” to --Schmidt--

Column 5
Line 3, change “anatomy experiment” to --an anatomy experiment--
Line 7, before “patient” insert --a--
Line 7, change “space” to --space,--
Line 10, change “to the symbols” to --the symbols--
Line 24, change “of vitreous” to --of the vitreous--
Line 28, change “cause” to --causes--
Line 34, change “When the healthy eyes” to --When healthy eyes--
Line 34, change “eyes adjustment” to --eye adjustment--
Line 35, change “concentration of eyes” to --concentration of the eyes--
Line 36, change “fovea of eyes” to --fovea of the eyes--
Line 37, change “adjustment of eyes” to --adjustment of the eyes--
Line 48, change “have provide” to --have provided--
Line 49, change “is resulted” to --results--
Line 53, change “cure the myopia” to --cure myopia--
Line 58, change “adjust” to --adjustment--
Line 61, change “long time and over” to --long time, over--

Column 6
Line 1, change “so that it can prevention and cure the myopia” to --so that it can prevent and cure myopia--
Line 2, change “Double vision marks combine” to --double vision marks combined--
Line 17, before “double” insert --a--
Line 19, before “double” insert --a--
Line 21, before “single” insert --a--
Line 23, before “double” insert --a--
Line 25, before “double” insert --a--
Line 31, after “Mark” insert --5—Control Key of LCD Gameboy--
Line 37, change “Anti Eyes Sight” to --Anti Eye Sight--
Line 47, change “is blocker frame” to --is a blocker frame--
Line 49, change “Track and rack 34” to --rack 34--
Line 51, change “through axis lever” to --through an axis lever--
Line 55, change “frication” to --friction--
Line 56, change “belt fasten structure” to --belt fastener structure--

Column 7
Line 1, change “baffle 8” to --spacer 8--
Line 4, change “about 4 D convex lens single let” to --about single 4D convex lens--
Line 9, change “concave” to --convex--
Line 16, change “is standing frame” to --is a standing frame--
Line 16, change “the anti eyes cross sight reflection” to --the anti eye sight interleave reflection--
Lines 19-20, change “Mechanical” to --A mechanical--
Line 23, change “is interior built vision mark illumination” to --is the interior built vision mark illuminating--
Line 26, change “of above stated methods.” to --of the above stated methods.--
Line 26, after “methods.” insert a carriage return
Line 31, change “1.5 hour” to --1.5 hours--
Line 33, change “improve 3 behavior” to --improve behavior--
Line 37, change “result” to --results--
Line 38, change “Diagram 1” to --Table 1--
Line 42, change “Diagram 2” to --Table 2--

Column 9
Line 8, change “the degree” to --is the degree--
Line 11, change “adjust” to --adjustment--

Column 10
Line 23, change “the” to --is the--
Line 27, change “adjust” to --adjustment--
Line 35, change “mechanism” to --mechanisms--

UNITED STATES PATENT AND TRADEMARK OFFICE

CERTIFICATE OF CORRECTION

PATENT NO. : 7,726,812 B2
APPLICATION NO. : 10/584355
DATED : June 1, 2010
INVENTOR(S) : Dai et al.

It is certified that error appears in the above-identified patent and that said Letters Patent is hereby corrected as shown below:

On the Title Page
Item 22, change the date from “Dec. 20, 2004” to --Dec. 24, 2004--
Item 86, change “PCT/CN2004/015114” to --PCT/CN2004/001514--
Item 30, change “2003 1 0109716” to --2003 1 0109716.7--
Item 30, change “2004 1 0098856” to --2004 1 0098856.3--

Signed and Sealed this
Twenty-eighth Day of June, 2011

David J. Kappos
*Director of the United States Patent and Trademark Office*